(12) United States Patent
Lee et al.

(10) Patent No.: US 8,476,055 B2
(45) Date of Patent: Jul. 2, 2013

(54) METHOD FOR PREPARING METAL NANOPARTICLE USING METAL BINDING PROTEIN

(75) Inventors: Sang Yup Lee, Daejeon (KR); Tae Jung Park, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 1057 days.

(21) Appl. No.: 12/301,581

(22) PCT Filed: Apr. 17, 2007

(86) PCT No.: PCT/KR2007/001865
§ 371 (c)(1),
(2), (4) Date: Jun. 10, 2009

(87) PCT Pub. No.: WO2007/136174
PCT Pub. Date: Nov. 29, 2007

(65) Prior Publication Data
US 2011/0124131 A1 May 26, 2011

(30) Foreign Application Priority Data
May 22, 2006 (KR) .................. 10-2006-0045455

(51) Int. Cl.
*C12N 1/20* (2006.01)
*C07H 21/04* (2006.01)
(52) U.S. Cl.
USPC ...... 435/252.1; 435/69.1; 536/23.1; 977/773; 977/810

(58) Field of Classification Search
None
See application file for complete search history.

(56) References Cited

U.S. PATENT DOCUMENTS

| 6,391,590 | B1 | 5/2002 | Sano et al. | |
|---|---|---|---|---|
| 6,489,537 | B1 * | 12/2002 | Rea et al. | 800/278 |
| 6,844,485 | B2 | 1/2005 | Butler et al. | |
| 7,022,628 | B2 | 4/2006 | Kim et al. | |

FOREIGN PATENT DOCUMENTS

| KR | 1020000032755 A | 6/2000 |
|---|---|---|
| KR | 1020040093978 A | 11/2004 |
| KR | 1020050007661 A | 1/2005 |
| KR | 1020050082581 A | 8/2005 |

OTHER PUBLICATIONS

Jovin, Thomas M., Quantum dots finally come of age, Nature Biotechnology, Jan. 2003, pp. 32-33, vol. 21.
Wu, Xingyong, et al., Immunofluorescent labeling of cancer marker Her2 and other cellular targets with semiconductor quantum dots, Nature Biotechnology, Jan. 2003, pp. 41-46, vol. 21.
Alivisatos, Paul, The use of nanocrystals in biological detection, Nature Biotechnology, Jan. 2004, pp. 47-52, vol. 22, No. 1.
Gao, Xiaohu, et al., In vivo cancer targeting and imaging with semiconductor quantum dots, Nature Biotechnology, Aug. 2004, pp. 969-976, vol. 22, No. 8.
Lidke, Diane, S., et al., Quantum dot ligands provide new insights into erbB/HER receptor-mediated signal transduction, Nature Biotechnology, Feb. 2004, pp. 198-203, vol. 22, No. 2.
Kim, Sungjee, et al., Near-infrared fluorescent type II quantum dots for sentinel lymph node mapping, Nature Biotechnology, Jan. 2004, pp. 93-97, vol. 22, No. 1.
Valls, Marc, et al., Exploiting the genetic and biochemical capacities of bacteria for the remediation of heavy metal pollution, FEMS Microbiology Reviews, (2002), pp. 327-338, vol. 26.
Cobbett, Christopher S., Phytochelatin biosynthesis and function in heavy-metal detoxification, Current Opinion in Plant Biology, 2000, pp. 211-216, vol. 3.
Hamer, Dean H., Metallothionein, Ann. Rev. Biochem, 1986, pp. 913-951, vol. 55.
Wu, Ching-Mei, et al., Immobilization of mettalothionein as a sensitive biosensor chip for the detection of metal ions by surface plasmon resonance, Biosensors & Bioelectronics, 2004, pp. 864-871, vol. 20.
Margoshes, Marvin, et al., A Cadmium Protein From Equine Kidney Cortex, J. Am. Chem. Soc., 1957, pp. 4813-4814, vol. 79.
Park, Si Jae, et al., Journal of Bacteriology, Sep. 2003, pp. 5391-5397, vol. 185, No. 18.
Bertini, Ivano, et al., High resolution solution of the protein part of Cu7 metallothionein, Eur. J. Biochem., 2000, pp. 1008-1018, vol. 267, No. 4.
Dameron, C.T., et al., Biosynthesis of cadmium sulphide quantum semiconductor crystallites, Letters to Nature, Apr. 13, 1989, vol. 338, pp. 596-597.
Kang, Seung Hyun, Engineered *E. coli* and its Application in Bioremediation and Nanotechnology, A Dissertation submitted in partial satisfaction of the requirements for the degree of Doctor of Philosophy in Chemical and Environmental Engineering, University of California Riverside, Jun. 2009.
Kim, Se-Kwon, et al., Selective Cadmium Accumulation Using Recombinant *Escherichia coli*, Journal of Bioscience and Bioengineering, 2005, pp. 109-114, vol. 99, No. 2.

(Continued)

*Primary Examiner* — Anand Desai
(74) *Attorney, Agent, or Firm* — Tristan A. Fuierer; Andrew D. Gerschutz; Moore & Van Allen, PLLC

(57) ABSTRACT

The present invention relates to a method of preparing heavy metal nanoparticles using a heavy metal-binding protein. More specifically, relates to a method for preparing heavy metal structures, comprising the steps of: culturing a microorganism transformed with a gene encoding a heavy metal-binding protein, in a heavy metal ion-containing medium, to produce heavy metal structures in the microorganism; and collecting the produced heavy metal structures, as well as nanoparticles of heavy metal structures prepared according to said method. Unlike prior methods of preparing quantum dots by physically binding metal materials, the quantum dots disclosed herein can be efficiently produced by expressing the heavy metal-binding protein in cells. In addition, the quantum dots are useful because they can solve an optical stability problem that is the shortcoming of organic fluorophores.

9 Claims, 6 Drawing Sheets

OTHER PUBLICATIONS

Mandal, Deendayal, et al., The use of microorganisms for the formation of metal nanoparticles and their application, Appl Microbiol Biotechnol, 2006, pp. 485-492, vol. 69.

Presta, Anthony, et al., Incorporation of Copper into the Yeast *Saccharomyces cerevisiae*. Identification of Cu(I)-Metallothionein in Intact Yeast Cells, J. Inorg. Biochem., Jun. 1997, pp. 231-240, vol. 66, No. 4.

Sauge-Merle, Sandrine, et al., Enhanced Toxic Metal Accumulation in Engineered Bacterial Cells Expressing Bacterial Cells Expressing *Arabidopsis thaliana* Phytochelatin Synthase, Applied and Environmental Microbiology, Jan. 2003, pp. 490-494, vol. 69, No. 1.

Sweeney, Rozamond Y., et al., Bacterial Biosynthesis of Cadmium Sulfide Nanocrystals, Chemistry & Biology, Nov. 2004, pp. 1553-1559, vol. 11.

Wawrzynska, Anna, et al., Overexpression of genes involved in phytochelatin biosynthesis in *Escherichia coli*: effects on growth, cadmium accumulation and thiol level, Acta Biochimica Polonica, 2005, pp. 109-116, vol. 52, No. 1.

European Patent Office, Supplementary European Search Report, PCT/KR2007/001865, Sep. 17, 2010.

Scarano, Gioacchino, et al, Properties of phytochelatin-coated CdS nanocrystallites formed in a marine phytoplanktonic alga (*Phaedactylum tricornutum*, Bohlin) in response to Cd, Plant Science, 2003, pp. 803-810, vol. 165.

Chinese Patent Office, Office Action, Nov. 1, 2010.

\* cited by examiner

METHOD FOR PREPARING METAL NANOPARTICLE USING METAL BINDING PROTEIN

CROSS-REFERENCE TO RELATED APPLICATIONS

This application is filed under the provisions of 35 U.S.C. §371 and claims the priority of International Patent Application No. PCT/KR2007/001865 filed on 17 Apr. 2007 entitled "Method for Preparing Metal Nanoparticle Using Metal Binding Protein" in the name of Sang Yup Lee, et al., which claims priority of Korean Patent Application No. 10-2006-0045455 filed on 22 May 2006, both of which are hereby incorporated by reference herein in their entirety.

TECHNICAL FIELD

The present invention relates to a method for preparing heavy metal nanoparticles using a heavy metal-binding protein, and more particularly to a method for preparing heavy metal structures, comprising the steps of culturing a microorganism, which is transformed with a gene encoding a heavy metal-binding protein, in a heavy metal ion-containing medium, to produce heavy metal structures in the microorganism, and collecting the produced heavy metal structures, as well as nanoparticles of heavy metal structures produced according to said method.

BACKGROUND ART

Quantum dots are nanometer-size semiconductor particles, which emit light when they are excited with energy such as light, and the color of the emitted light depends on the size of the particles. That is, when the size of the particles is decreased to reduce the dimension of the particles, the electronic state density and energy thereof will be varied, and thus the characteristics of the particles will vary depending on the dimension thereof. For example, quantum hall effect, which does not appear in three-dimensional systems, is observed in two-dimensional systems. As used herein, the term "reducing dimension" in the strict sense means that electrons are confined to an area smaller than the de Broglie wavelength. A zero-dimensional quantum dot is not a dot having no area, but rather refers to a sample having a three-dimensional size smaller than the de Broglie wavelength. In quantum mechanics, a wave in all material particles with momentum, that is, the de Broglie wavelength, varies depending on material and is about 10 nm for semiconductor material.

As shown in FIG. 1, a quantum dot is generally in the form of a sphere consisting of a core and a shell and contains, in addition to Zn, S and Cd illustrated in FIG. 1, other various heavy metals.

Methods for preparing quantum dots can be broadly divided into two categories: lithographic methods using a light source such as a laser; and chemical synthesis methods. The synthesis of quantum dots by chemical method has an advantage in that it can produce quantum dots using a relatively simple system compared to the lithographic method, but this method still has a lot of technical problems to be solved in order to produce a large amount of quantum dots in a cost-effective manner. Also, in comparison with quantum dots prepared using the prior bulk method, quantum dots prepared using molecular chemical technique have excellent optical stability, and their optical properties can be controlled so as to emit light at various wavelengths depending on the size, shape and component of nanomaterials. For this reason, it has become possible to apply quantum dot-based nanomaterials in the biological field. This indicates that the quantum dot-based nanomaterials can be widely used as not only biosensors, but also contrast agents for in vivo optical imaging, and the possibility thereof has recently been proven through various studies (Jovin, *Nat. Biotechnol.*, 21:32, 2003; Wu et al., *Nat. Biotechnol.*, 21:41, 2003; Alivisatos, *Nat. Biotechnol.*, 22:47, 2004; Gao et al., *Nat. Biotechnol.*, 22:969, 2004; Lidke et al., *Nat. Biotechnol.*, 22:198, 2004).

As typical examples thereof, techniques capable of tracking the signal transduction of live cells in vitro were developed, and one example thereof is an approach to the HER2/neu pathway. This overcomes the shortcoming of existing organic fluorophores, in that they readily lose their optical stability, such that they cannot track continuous cell changes (Wu et al., *Nat. Biotechnol.*, 21:41, 2003; Lidke et al., *Nat. Biotechnol.*, 22:198, 2004). Also, in order to track erbB/HER receptor-mediated signal transduction in live cells, an epidermal growth factor (EGF) was conjugated to quantum dots and activated through binding to an epidermal growth factor receptor (EGFR). Then, the process of incorporation of the quantum dot conjugate-conjugated EGFR into cells was tracked (Lidke et al., *Nat. Biotechnol.*, 22:198, 2004). This method enabled biological processes in live cells to be observed in real time.

Furthermore, to overcome a shortcoming of insufficient in vivo permeability, semiconductor nanocrystals, which can use wavelengths in the near infrared range, were developed, thus making in vivo image acquisition possible (Gao et al., *Nat. Biotechnol.*, 22:969, 2004). In this method, in order to effectively make quantum dots soluble and, at the same time, effectively deliver quantum dots in vivo, quantum dots (ZnS-capped CdSe) were coated with a triblock copolymer, and a monoclonal antibody is conjugated to the reactive group of the coated polymer.

In addition, to overcome a shortcoming of low in vivo permeability of optical imaging, quantum dots, which can be adjusted to the near infrared wavelength, were developed. For example, quantum dots having the near infrared wavelength were used to optically image the sentinel lymph node in the armpit of mice (Kim et al., *Nat. Biotechnol.*, 22:93, 2004). Such nanomaterials show physical properties different from those of the bulk method as shown in quantum dots, and thus have the potentiality to be used in magnetic resonance imaging.

Meanwhile, methods for treating metal ions in the environment generally include chemical, physical and biological treatment methods. The biological treatment method employs the biological mechanisms of microorganisms themselves, and microbial mechanisms, including biosorption & bioaccumulation, oxidation & reduction, metal-organic complexation and insoluble complex formation, provide an important technical foundation for restoring the environment contaminated with heavy metal (Valls and de Lorenzo, *FEMS Microbiol. Rev.*, 26:327, 2002). Furthermore, with the development of molecular biology, a recent attempt to develop strains having an increased ability to bind heavy metals suggests the possibility to improve prior biological treatment methods. Microorganisms synthesize heavy metal-binding proteins to remove heavy metals in vivo and ex vivo through bioaccumulation, and these proteins are involved in the storage or regulation of concentration of intracellular metal ions.

Recently, it was found that peptides, called phytochelatins, which naturally bind to harmful elements, such as lead, mercury and cadmium, to detoxify these elements, are produced by fungi and plants, exposed to heavy metals. Phytochelatins have a structure of (gamma-Glu-Cys)n-Gly (n=2-7) and accumulate metal ions through the formation of peptide-metal conjugates (Cobbett, *Curr. Opin. Plant Biol.*, 3:211, 2000). In addition, as other kinds of heavy metal-binding proteins, low-molecular proteins called metallothioneins have been much studied, and these proteins have a high content of cysteine and bind to cadmium, zinc, nickel, copper and the like (Hamer, *Annu. Rev. Biochem.*, 55:913, 1986; Wu and Lin, *Biosens. Bioelectron.*, 20:864, 2004).

Meanwhile, patent documents relating to the preparation of quantum dots include: Korean Patent Registration No. 10-0540801, entitled "Method of preparing quantum dots using metal powder"; Korean Patent Registration No. 10-0526828, entitled "Method of preparing quantum dots having uniform distribution by irradiating magnetic membrane or semiconductor membrane with laser"; Korean Patent Registration No. 10-0541516, entitled "Method for forming quantum dots of semiconductor material"; and Korean Patent Registration No. 10-0279739, entitled "Method for forming nanometer-size silicon quantum dots. However, these methods are methods of preparing quantum dots through the physical binding of metal materials.

Having paid attention to that the component of a quantum dot is synthesized by a regular arrangement of cadmium (Cd), selenium (Se), zinc (Zn) and tellurium (Te), the present inventors expressed a heavy metal-binding protein using a bioengineering method. As a result, the present inventors have found that it is possible to synthesize highly economical quantum dots in vivo, and also used the above biological system to prepare quantum dots having optical stability, thereby completing the present invention.

SUMMARY OF THE INVENTION

It is therefore an object of the present invention to provide a recombinant microorganism having the ability to produce heavy-metal structures, and a method for preparing nanoparticles of heavy-metal structures, which comprises culturing the recombinant microorganism in a heavy metal ion-containing medium.

Another object of the present invention is to provide a method for improving nanoparticles, which comprises binding the nanoparticles to at least one selected from the group consisting of chemical materials, ligands, metals, DNAs and proteins.

In order to achieve the above-mentioned objects, the present invention provides a method for preparing nanoparticles of heavy metal structures, the method comprising the steps of: culturing a microorganism, which is transformed with a gene encoding one or multi heavy metal-binding proteins, in a heavy metal ions-containing medium, to produce heavy metal structures in the microorganism; and collecting the produced heavy metal structures.

The present invention also provides nanoparticles of heavy metal structures, which are prepared according to said method, have a diameter of 5-120 nm and are in the form of spheres.

The present invention also provides a recombinant microorganism having the ability to produce heavy metal structures, the microorganism being transformed with an expression vector containing a heavy metal-binding protein-encoding gene or a portion thereof.

The present invention also provides a method for improving nanoparticles, the method comprises binding the nanoparticles to at least one selected from the group consisting of chemical materials, ligands, metals, DNAs and proteins.

The present invention also provides a method for improving nanoparticles, the method comprises binding a protein to the nanoparticles, and treating the bound protein with a protein recognizing a material labeling the bound protein, a labeled ligand binding to the target protein, or an antibody binding specifically to the target protein.

The present invention also provides a method for improving nanoparticles, the method comprising the steps of: (a) coating biotin on the surface of the nanoparticles; (b) coating streptavidin on the biotin-coated surface; (c) modifying the streptavidin-coated surface with at least one chemical residue selected from the group consisting of amine, aldehyde and carboxyl groups; and (d) coating the modified surface with gold or silver.

Another features and embodiments of the present invention will be more clarified from the following "detailed description" and the appended "claims".

BRIEF DESCRIPTION OF DRAWINGS

In FIG. 5, "a": *E. coli* cells showing blue fluorescence coincident with a light emission spectrum of 420 nm; "b": *E. coli* cells showing yellow fluorescence having an emission spectrum of 700 nm; "c": real image; and "d": a merge image of "a" and "b". Also, all scale bars in the figure represent 5 μm.

In FIG. 6, "a": a control group which did not express phytochelatin synthase; and b-d: TEM images at various magnifications of heavy metal structures accumulated in *E. coli* cells expressing phytochelatin synthase, according to the present invention.

DETAILED DESCRIPTION OF THE INVENTION, AND PREFERRED EMBODIMENTS

Figure 1:
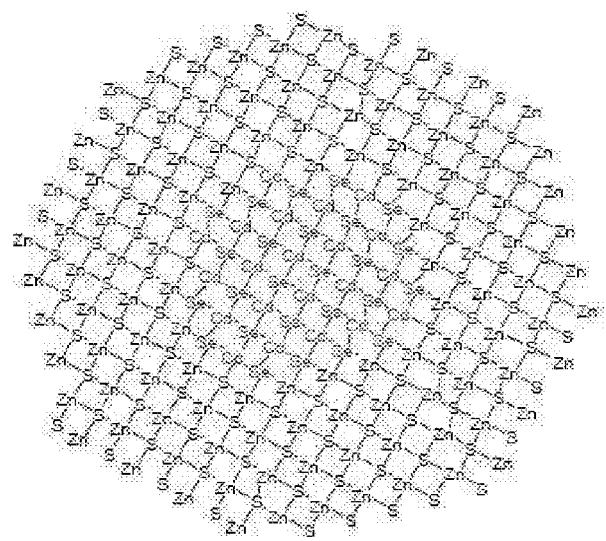
FIG. 1 illustrates the general structure of quantum dots.

In the present invention, in order to introduce and express a heavy metal-binding protein gene in *E. coli* and then synthesize quantum dots depending on the adsorption and accumulation of heavy metals by the expression of the metal-binding protein in the *E. coli* cells, a plasmid was constructed such that phytochelatin synthase- and metallothionein-encoding genes, encoding heavy metal-binding proteins, would be expressed alone or in combination. Then, *E. coli* was transformed with the plasmid and cultured to produce heavy metal-binding protein in the cells, the cells were then cultivated in media containing each of heavy metal ions, and whether the heavy metal structures synthesized in the cells would be quantum dots was examined by qualitative analysis and fluorescence analysis.

In one aspect, the present invention relates to a method for preparing nanoparticles of heavy metal structures, the method comprising the steps of: culturing a microorganism, which is transformed with a gene encoding a heavy metal-binding protein, in a heavy metal ion-containing medium, to produce heavy metal structures in the microorganism; and collecting the produced heavy metal structures, as well as nanoparticles of heavy metal structures, which are prepared according to said method, have a diameter of 5-120 nm and are in the form of spheres.

In the present invention, the heavy metal structures are preferably nanoparticles, and the nanoparticles are preferably quantum dots.

In the present invention, the heavy metal-binding protein can be derived from any one selected from the group consisting of *Homo sapiens, Arabidopsis thaliana, Ornamental tobacco, Mus musculus, Saccharomyces cerevisiae, Schizosaccharomyces pombe, Pseudomonas putida* and *Escherichia coli*, but the scope of the present invention is not limited thereto.

In the present invention, phytochelatin synthase and metallothionein were illustrated as heavy metal-binding proteins, but it will be obvious to one skilled in the art that other proteins or peptides having properties equal or similar to those of said proteins may also be used in the present invention.

In another aspect, the present invention relates to a recombinant microorganism having the ability to produce heavy metal structures, the microorganism being transformed with an expression vector containing a heavy metal-binding protein-encoding gene or a portion thereof.

In the present invention, the heavy metal-binding protein is preferably phytochelatin synthase or metallothionein, and a portion of a gene encoding said phytochelatin synthase preferably has a base sequence of SEQ ID NO: 5.

The method of the present invention comprises a step of culturing *E. coli* transformed with a recombinant vector, which expresses *Arabidopsis thaliana*-derived phytochelatin synthase and *Pseudomonas putida*-derived metallothionein alone or in combination, to express a heavy metal-binding protein in the *E. coli* cells. In the present invention, the heavy metal-binding protein is preferably fused to the C-terminal or N-terminal end of said protein.

Specific examples of heavy metals for use in the present invention include cadmium (Cd), zinc (Zn), selenium (Se), tellurium (Te), cesium (Cs), copper (Cu), chlorine (Cl), lead (Pb), nickel (Ni), manganese (Mn), mercury (Hg), cobalt (Co) and chromium (Cr).

Recombinant plasmid pTJ1-AtPCS, which is used in an embodiment of the present invention to transform *E. coli* so as to express phytochelatin synthase, comprises a phytochelatin synthase-encoding gene, an ampicillin-resistance gene, and a trc promoter for expression induction. In order to express phytochelatin synthase in *E. coli*, a phytochelatin synthase protein-encoding gene was constructed by synthesizing two primers from a base sequence (cDNA) complementary to the chromosomal DNA of *A. thaliana* and performing PCR using the primers. Also, a fusion gene of phytochelatin synthase and metallothionein was constructed by obtaining a heavy metal-binding gene of metallothionein from the chromosomal DNA of *P. putida* by PCR using a base sequence deposited in the GenBank and subjecting the gene to overlapping PCR. Also, an ampicillin-resistance gene can be used for strain screening.

The phytochelatin synthase and metallothionein obtained from the strain was expressed alone or in combination, and the cells containing the protein expressed therein were cultured in a heavy metal-containing medium and observed at each of growth stages and each of heavy metal concentrations. As a result, it could be seen that heavy metals were adsorbed and accumulated in the cells to form quantum dots having a regular arrangement. From the quantum dots in vivo, quantum dots could be readily collected by subjecting the in vivo quantum dots to a simple cell disruption process and filtering the disrupted cells through a membrane having a pore size of a few hundreds of nanometers.

It will be obvious to one skilled in the art that not only the above-described heavy metal-binding proteins, but also all intracellular components, to which heavy metals can bind, including proteins, DNAs, intermediates and metabolites, can be used in the present invention without limitation to examples of the present invention. Various heavy metal-binding proteins are found in a wide range from higher organisms to microorganisms, and the heavy metal-binding protein was found for the first time in equine kidney cells (Margoshe and Vallee, *J. Am. Chem. Soc.*, 79:4813, 1957). Typical species currently known in the literature include *Homo sapiens, Arabidopsis thaliana, Ornamental tobacco, Mus musculus, Saccharomyces cerevisiae, Schizosaccharomyces pombe, Pseudomonas putida*, and *Escherichia coli*. Thus, it will be obvious to one skilled in the art that various heavy metal-binding regions can be used in the present invention.

In the present invention, the microorganism is preferably selected from the group consisting of gram-positive bacteria, gram-negative bacteria, Actinomycetes, yeasts and fungi. In the present invention, the recombinant microorganism is preferably *E. coli*.

In the present invention, the microorganism is preferably modified such that it does not produce intracellular and extracellular proteases, which are involved in the degradation of an expressed protein, so as to be advantageous for the intracellular expression of the heavy metal-binding protein.

In the present invention, the expression vector containing a heavy metal-binding protein-encoding gene or a portion thereof preferably has a deletion or location-specific mutation of a portion of the amino acid sequence of the heavy metal-binding protein, such that the heavy metal-binding protein is advantageous for heavy metal binding.

Figure 2:
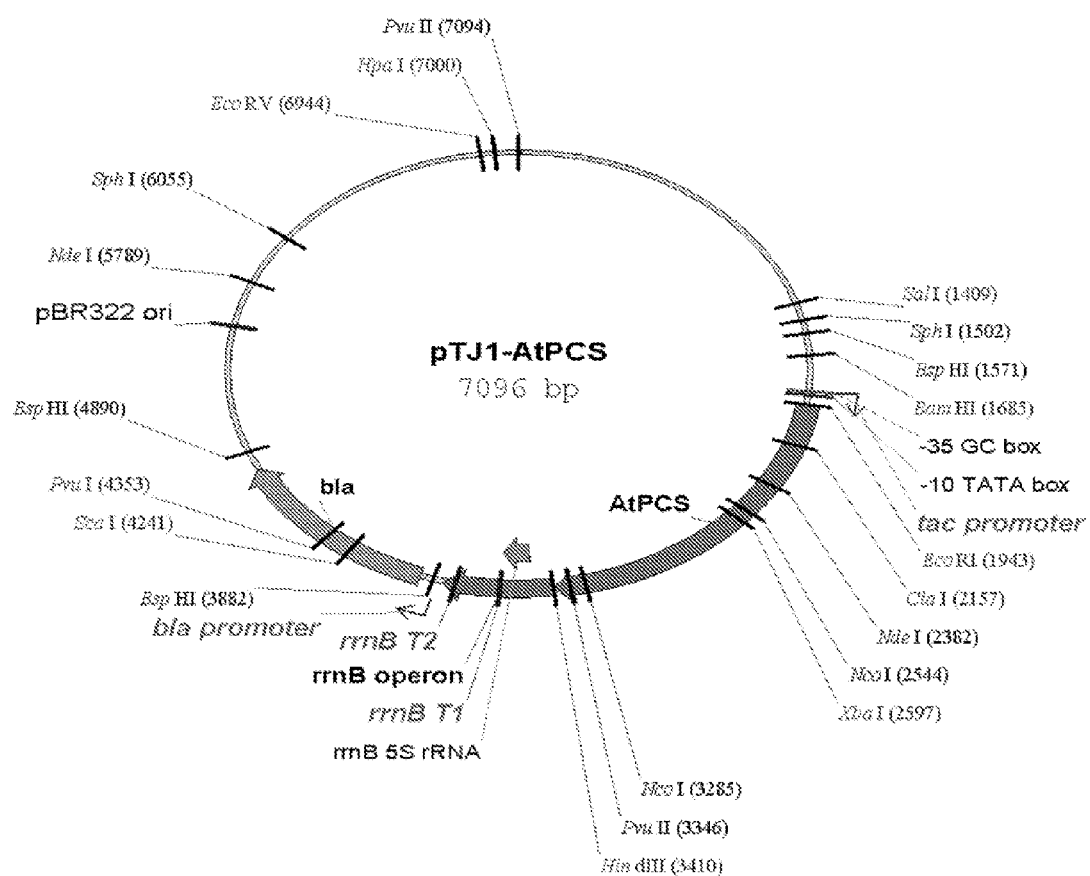
FIG. 2 is a genetic map of expression vector pTJ1-AtPCS according to the present invention.

In the present invention, the expression vector containing a heavy metal-binding protein-encoding gene or a portion thereof is preferably pTJ1-AtPCS having a cleavage map of FIG. 2. Also, the expression vector containing a heavy metal-binding protein-encoding gene or a portion thereof is preferably pTJ1-PpMT having a cleavage map of FIG. 3.

The nanoparticles of heavy metal structures according to the present invention readily bind to various chemical materials or biomaterials, and thus can be improved for various purposes. Accordingly, in another aspect, the present invention relates to a method for improving nanoparticles, which comprises binding the nanoparticles to at least one selected from the group consisting of chemical materials, ligands, metals, DNAs and proteins.

In one embodiment, the nanoparticles according to the present invention can be improved by binding a protein to the nanoparticles, and treating the bound protein with a protein recognizing a material labeling the bound protein, a labeled ligand binding to the target protein, or an antibody binding specifically to the target protein.

In another embodiment, the nanoparticles according to the present invention can be improved through a method comprising the steps of: (a) coating biotin on the surface of the nanoparticles; (b) coating streptavidin on the biotin-coated surface; (c) modifying the streptavidin-coated surface with at least one chemical residue selected from the group consisting of amine, aldehyde and carboxyl groups; and (d) coating the modified surface with gold or silver.

EXAMPLES

Hereinafter, the present invention will be described in further detail with reference to examples. It will however be obvious to one skilled in the art that these examples are provided to more fully explain the present invention, and the scope of the present invention is not limited thereto.

Example 1

Preparation of Expression Vector of Heavy Metal-Binding Protein (1) Preparation of Expression Vector of Phytochelatin Synthase In order to obtain an AtPCS gene (NCBI accession No. AF461180) that synthesize phytochelatin synthase, PCR was performed using, as template DNA, complementary DNA (cDNA) of *A. thaliana* represented by a base sequence of SEQ ID NO: 5 (*A. thaliana* phytochelatin synthase) and using primers of SEQ ID NO: 1 and SEQ ID NO: 2. The PCR reaction was performed in the following conditions: initial denaturation at 94° C. for 7 min; 30 cycles of denaturation at 94° C. for 1 min, annealing at 55° C. for 1 min and extension at 72° C. for 1 min; and then final extension at 72° C. for 7 min.

SEQ ID NO: 1: 5'-GGAATTCATGGCTATGGCGAGTTTAT-3'

SEQ ID NO: 2: 5'-CCCAAGCTTATTAATAGGCAGGAGCAGCGAG-3'

An about 1.5-kb DNA fragment obtained by the PCR reaction was separated using an agarose gel electrophoresis method and cut with two restriction enzymes EcoRI and HindIII. At the same time, plasmid pTac99A (Park and Lee, *J. Bacteriol.*, 185:5391, 2003) having a strong inducible tac promoter was cut with two restriction enzymes EcoRI and HindIII. Then, the plasmid was combined and ligated to the DNA fragment by T4 DNA ligase, and the ligated plasmid was transformed into *E. coli* DH5α by electroporation. The transformed strain was screened on an LB plate medium containing antibiotic ampicillin (100 µg/L), thus obtaining a pTJ1-AtPCS recombinant plasmid (FIG. 2). In the prepared recombinant plasmid pTJ1-AtPCS, the AtPCS gene to be used as a heavy metal-binding protein could be expressed by a strong inducible tac promoter.

(2) Preparation of Expression Vector of Metallothionein

In order to obtain a PpMT gene (NCBI accession No. NC_002947 REGION: 3696753.3696977) that synthesizes metallothionein, PCR was performed using, as template DNA, genomic DNA of *P. putida* KT2440 represented by a base sequence of SEQ ID NO: 6 (*P. putida* KT2440 metallothionein) and using primers of SEQ ID NO: 3 and SEQ ID NO: 4. The PCR reaction was performed in the following conditions: Initial denaturation at 94° C. for 7 min; 30 cycles of denaturation at 94° C. for 1 min, annealing at 55° C. for 1 min and extension at 72° C. for 1 min; and then final extension at 72° C. for 7 min.

SEQ ID NO: 3:   5'-GGAATTCATGAACGATCAACGCTGCGC-3'

SEQ ID NO: 4:   5'-AACTGCAGTTAGGGCGAGATCGGATCACT-3'

Figure 3:
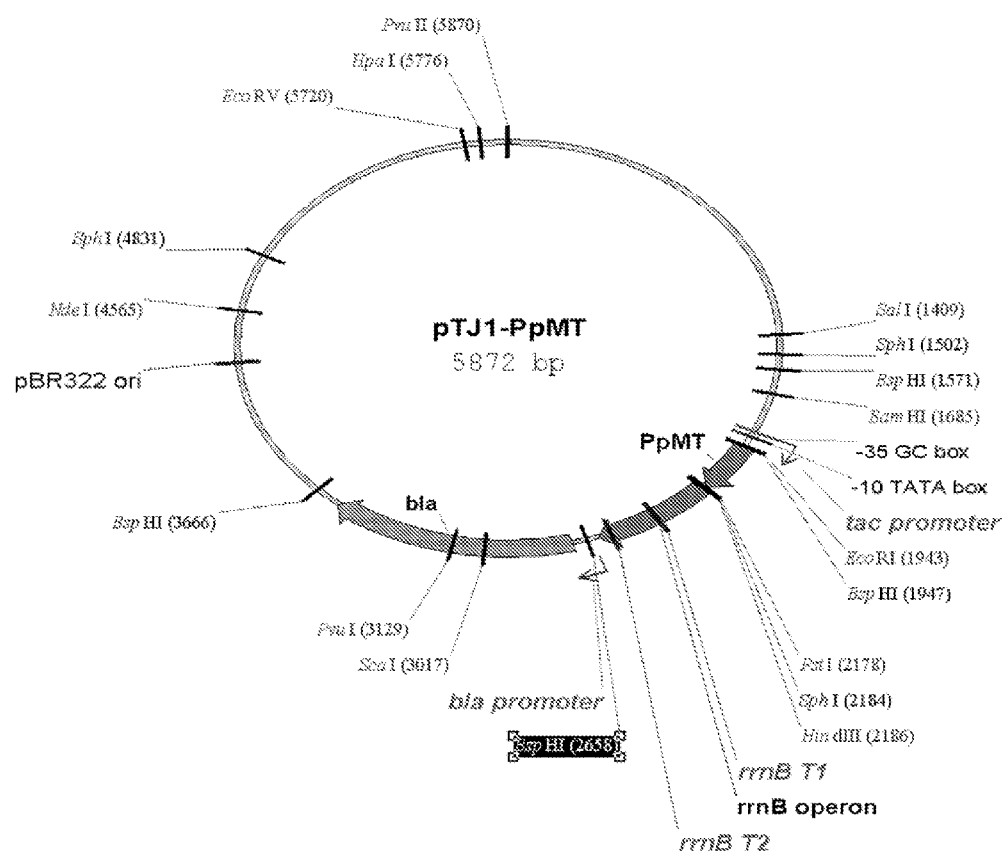
FIG. 3 is a genetic map of expression vector pTJ1-PpMT according to the present invention.

An about 230 bp DNA fragment obtained by the PCR reaction was separated using an agarose gel electrophoresis method and cut with two restriction enzymes EcoRI and PstI. At the same time, plasmid pTac99A having a strong inducible tac promoter was cut with two restriction enzymes EcoRI and PstI. Then, the plasmid was combined and ligated with the DNA fragment by T4 DNA ligase, and the ligated plasmid was transformed into *E. coli* DH5α by electroporation. The transformed strain was screened on an LB plate medium containing antibiotic ampicillin (100 µg/L), thus obtaining a pTJ1-PpMT recombinant plasmid (FIG. 3). In the prepared recombinant plasmid pTJ1-PpMT, the PpMT gene to be used as a heavy metal-binding protein could be expressed by a strong inducible tac promoter.

As host cells for expressing recombinant proteins, procaryotic cells, such as *E. coli* and *Bacillus subtillis*, which can be cultured at a high concentration within a short time, easily genetically modified and have well established physiological properties, have been widely used. However, to solve various problems, including the post-translational modification, secretion, three-dimensional active structure and activation of proteins, a wide range from microorganisms to higher organisms, including unicellular eukaryotic cells, yeasts (*Pichia pastoris, Saccharomyces cerevisiae, Hansenula polymorpha*, etc.), filamentous fungi, insect cells, plant cells, and mammalian cells, has recently been used as host cells for protein production. Thus, it will be obvious to one skilled in the art to use not only *E. coli* cells illustrated in Examples, but also other host cells.

Example 2

Fluorescence Analysis of *E. coli* Expressing Recombinant Plasmid pTJ1-AtPCS

Figure 4:
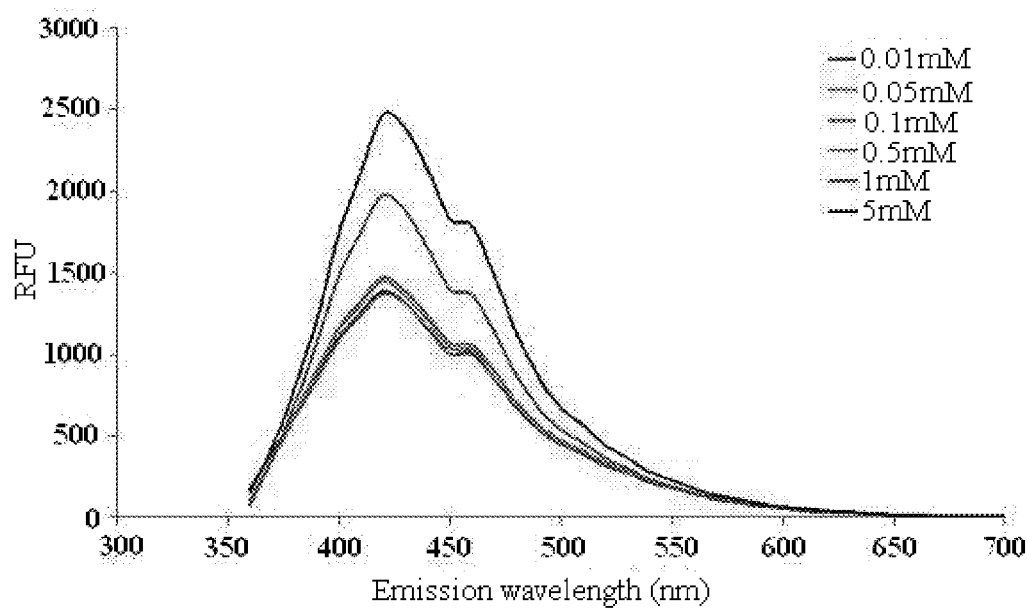
FIG. 4 shows the results of fluorescent scanning of *E. coli* expressing phytochelatin synthase in a medium containing heavy metal ions, such as cadmium, zinc and cesium.

Phytochelatin synthase was prepared by culturing *E. coli* DH5α transformed with recombinant plasmid pTJ1-AtPCS having a strong inducible tac promoter. For this purpose, the transformed *E. coli* was seeded into a 500 mL flask containing 100 mL of LB liquid medium containing heavy metal ions (5 mM $CdCl_2 \cdot 2.5H_2O$, $ZnCl_2$, $SeO_2$, $TeCl_4$, and $CsCl_2$) and cultured at 37° C. The pTJ1-AtPCS recombinant plasmid had the tac promoter, and thus IPTG was added to induce gene expression. For this, when the optical density (OD) of the medium reached 0.6 as measured at a 600-nm wavelength with a spectrophotometer, 1 mM IPTG was added to induce gene expression. At 4 hours after the induction of expression, the culture broth was centrifuged at 4° C. and 6000 rpm for 5 minutes. Then, the supernatant was discarded, and the remnant was washed one time with 10 mL PBS buffer (pH 7.4), centrifuged again at 4° C. and 6000 rpm for 5 minutes and then suspended in 10 mL PBS buffer. 100 µL of the suspended sample was dispensed into each well of a 96-well black plate and analyzed for emission spectra at 360-700 nm using a fluorescent spectrophotometer (Molecular Devices, USA) (FIG. 4). As shown in FIG. 4, it could be seen that a fluorescent signal having peak emission spectrum of about 420 nm strongly appeared at UV excitation of 320 nm. This suggests that materials having a characteristic fluorescent signal that quantum dots generate were included in the *E. coli* strain.

Figure 5:
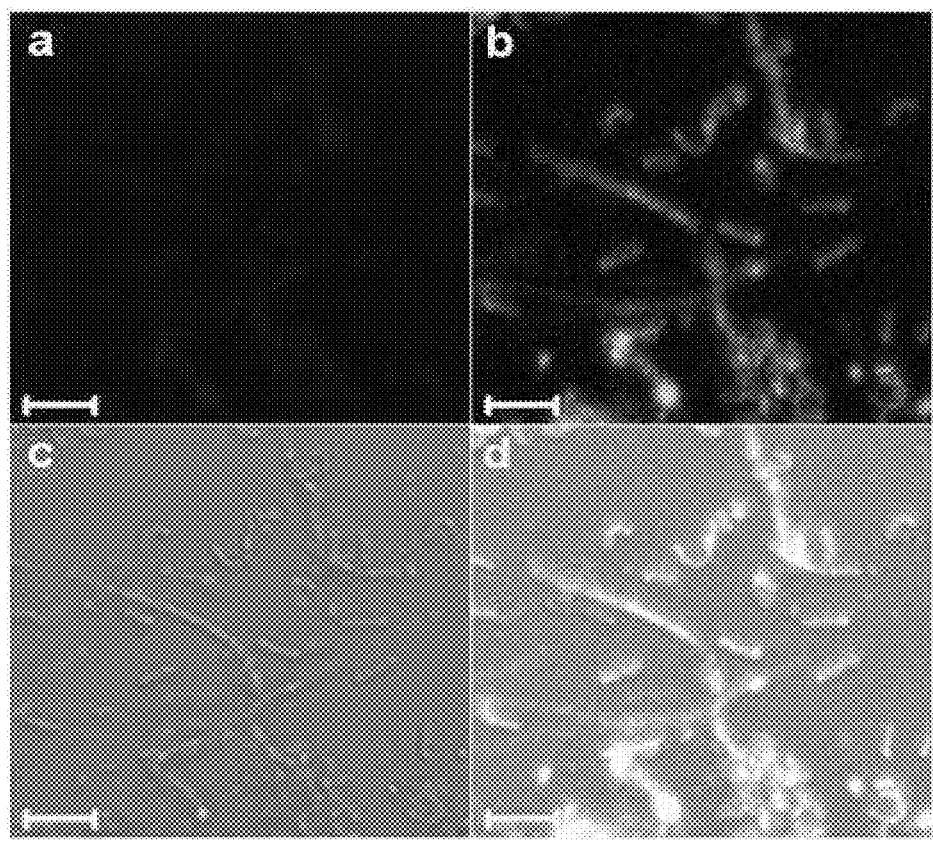
FIG. 5 shows confocal laser scanning microscopy images of heavy-metal structures accumulated in *E. coli* cells expressing phytochelatin synthase, according to the present invention.

Also, the *E. coli* strain expressing phytochelatin synthase was washed with distilled water, immobilized on a poly-L-lysine-coated slide glass and covered with a cover glass. Then, the fluorescent images of heavy metals accumulated in the cells were analyzed using a confocal laser scanning microscopy (LSM 510, Carl Zeiss, Germany) (FIG. 5). As a result, as shown in FIG. 5, blue fluorescence (a) coincident with an emission spectrum of about 420 nm shown in FIG. 4, and yellow fluorescence (b) having an emission spectrum of about 700 nm, could be observed in the *E. coli* cells. Thus, the characteristic fluorescence of nanoparticles such as quantum dots could also be observed in the intracellular heavy metal structures of the present invention. In FIG. 5, (c) is a real image, and (d) indicates a merge image of (a) and (b). Also, all scale bars shown in the figure represent 5 μm.

Example 3

Figure 6:
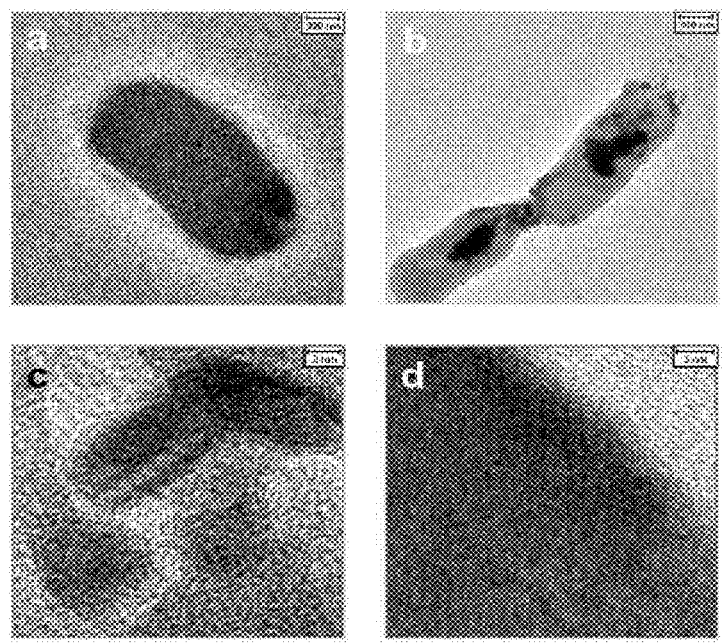
FIG. 6 shows transmission electron microscopy (TEM) images of heavy metal structures accumulated in *E. coli* cells expressing phytochelatin synthase, according to the present invention.

Characterization of in vivo Heavy Metals Synthesized in *E. coli* Expressing Recombinant Plasmid pTJ1-AtPCS In order to confirm whether phytochelatin synthase expressed by IPTG would make heavy metal structures in *E. coli* DH5α transformed with recombinant plasmid pTJ1-At-PCS having an inducible tac promoter, the *E. coli* of Example 2 was washed with distilled water and dried in a freeze dryer in a vacuum state for one day, and heavy metal accumulated in the cells were analyzed using a TEM (Technai G2, FEI, the Netherlands). As a result, it was seen that the size and shape of the heavy metal structures were uniform (FIG. 6). Also, it could be observed that heavy metal structures, which were not found in the control group (a) having no phytochelatin synthase expressed therein, were present in the *E. coli* having phytochelatin synthase expressed therein (FIGS. 6b, 6c and 6d).

The size of the heavy metal particles synthesized in the cells was about 5-120 nm as could be determined by the scale bar of the figure, but the scope of the present invention is not limited to this size and it is possible to prepare heavy metal particles having various sizes. Also, it could be seen that lattice-like structures, which are the characteristic structures of heavy metal nanoparticles, were formed in the *E. coli* cells (FIGS. 6c and 6d).

Moreover, heavy metal structures adsorbed in *E. coli* cells expressing phytochelatin synthase were analyzed by EDS using a TEM (Technai G2, FEI, the Netherlands). Herein, heavy metal structures in a portion marked on the microphotograph were analyzed and, as a result, among the components added to the medium, cadmium (Cd), zinc (Zn) and cesium (Cs) were detected (FIG. 7).

Figure 7:
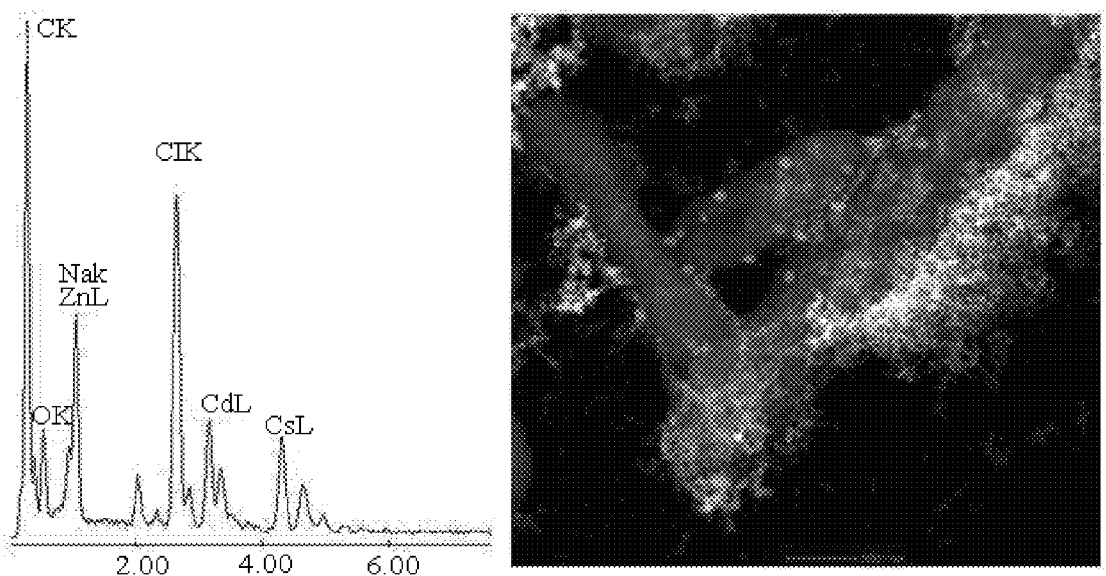
FIG. 7 shows the results of energy dispersive X-ray spectrometry (EDS) and TEM analysis of heavy metal structures accumulated in cells when *E. coli* expressing phytochelatin synthase was cultured in a medium containing cadmium (Cd), zinc (Zn) and cesium (Cs) ions, according to the present invention.

FIG. 7 shows the results of EDS and TEM analysis of heavy metal structures accumulated in cells when *E. coli* having phytochelatin synthase expressed therein was cultured in a medium containing 5 mM of each of cadmium (Cd), zinc (Zn) and cesium (Cs), according to the present invention. As shown in FIG. 7, it could be seen that, except for carbon (C) and oxygen (O), which can appear in organism *E. coli*, and also sodium (Na) and chlorine (Cl), which are always present in the *E. coli* cells, zinc (Zn), cadmium (Cd) and cesium (Cs) were the components of heavy metal nanoparticles in the cells.

Figure 8:
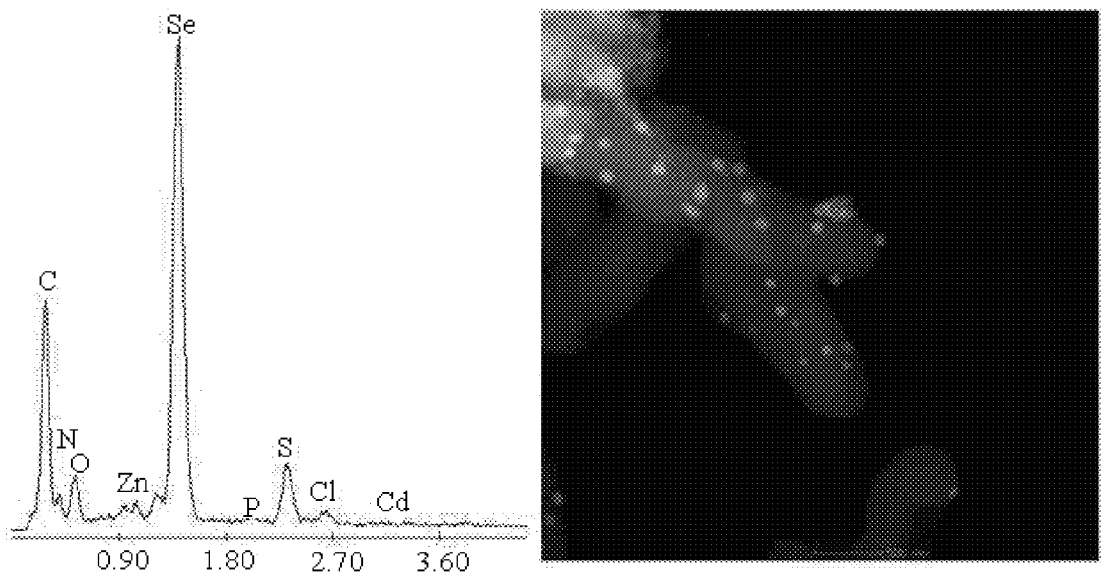
FIG. 8 shows the results of energy dispersive EDS and TEM analysis of heavy metal structures accumulated in cells when *E. coli* expressing phytochelatin synthase was cultured in a medium containing cadmium (Cd), zinc (Zn) and selenium (Se) ions, according to the present invention.

FIG. 8 shows the results of EDS and TEM analysis of heavy metal structures accumulated in cells when *E. coli* expressing phytochelatin synthase was cultured in a medium containing 5 mM of each of cadmium (Cd), zinc (Zn) and selenium (Se), according to the present invention. Particularly, heavy metal structures in a portion marked on the electron microphotograph were analyzed and, as a result, it was seen that the structures contained zinc (Zn) and selenium (Se) and had a high content of selenium (Se).

Figure 9:
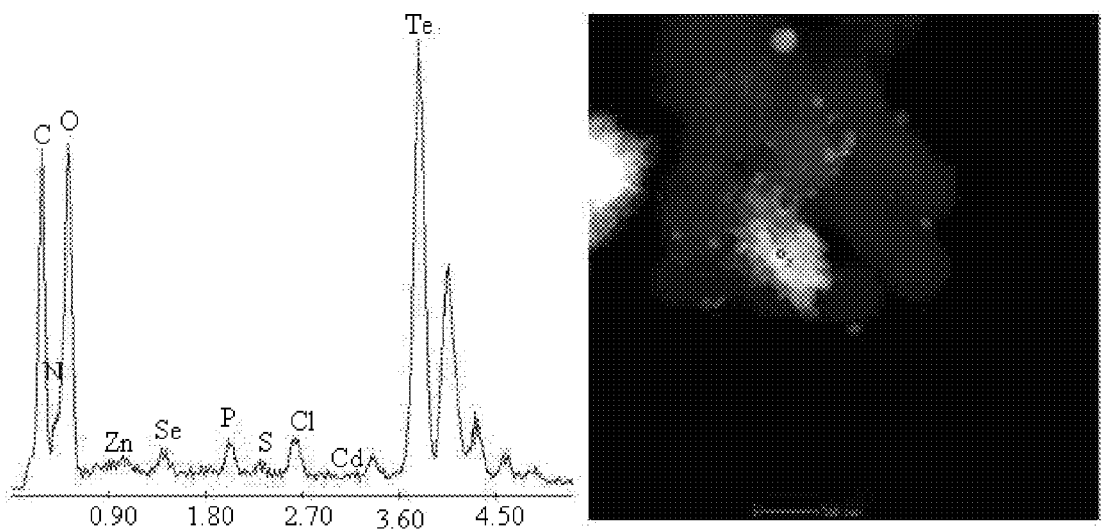
FIG. 9 shows the results of energy dispersive EDS and TEM analysis of heavy metal structures accumulated in cells when *E. coli* expressing phytochelatin synthase was cultured in a medium containing cadmium (Cd), zinc (Zn) and tellurium (Te) ions, according to the present invention.

FIG. 9 shows the results of EDS and TEM analysis of heavy metal structures accumulated in cells when *E. coli* expressing phytochelatin synthase was cultured in a medium containing 5 mM of each of cadmium (Cd), zinc (Zn) and tellurium (Te), according to the present invention. Heavy metal structures in a portion marked on the electron microphotograph were analyzed and, as a result, the heavy metal structures contained a small amount of zinc (Zn), selenium (Se) and cadmium (Cd) and had a high content of tellurium (Te).

The size of intracellular heavy metal nanoparticles used in the EDS of FIGS. 7 to 9 was about 30-50 nm. In addition, it could be observed through a TEM that heavy metal particles having various sizes from about 5 nm to about 120 nm were present in the cells.

INDUSTRIAL APPLICABILITY

As described and proven in detail above, the present invention provides the method of preparing heavy metal structures using a heavy metal-binding protein, quantum dots as nanoparticles prepared according to said method, and a recombinant microorganism having the ability to produce heavy metal structures, the recombinant microorganism being transformed with an expression vector containing a metal-binding protein-encoding gene or a portion thereof. Unlike the prior method of preparing quantum dots by physically binding metal materials, in vivo quantum dots as nanoparticles, which are provided according the present invention, are synthesized by the activity of an enzyme expressed in vivo. According to the present invention, the quantum dots can be produced with high productivity through a simple process in an efficient and cost-effective manner. In addition, the quantum dots are useful because they can solve an optical stability problem that is the shortcoming of organic fluorophores.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A recombinant microorganism having the ability to produce quantum dots, the microorganism being transformed with an expression vector containing a heavy metal-binding protein-encoding gene or a portion thereof, wherein the heavy metal-binding protein is phytochelatin synthase, wherein the expression vector containing a heavy metal-binding protein-encoding gene is pTJ1-AtPCS having a cleavage map of FIG. 2 or pTJ1-PpMT having a cleavage map of FIG. 3.

2. The recombinant microorganism having the ability to produce quantum dots according to claim 1, wherein the heavy metal is one or more selected from the group consisting of cadmium (Cd), zinc (Zn), selenium (Se), tellurium (Te), cesium (Cs), copper (Cu), lead (Pb), nickel (Ni), manganese (Mn), mercury (Hg), cobalt (Co) and chromium (Cr).

3. The recombinant microorganism having the ability to produce heavy metal quantum dots according to claim 1, wherein the portion of a gene encoding said phytochelatin synthase has a base sequence of SEQ ID NO: 5.

4. The recombinant microorganism having the ability to produce heavy metal quantum dots according to claim 1, wherein the microorganism is selected from the group consisting of gram-positive bacteria, gram-negative bacteria, Actinomycetes, and fungi.

5. The recombinant microorganism having the ability to produce heavy metal quantum dots according to claim 1, wherein the microorganism is *E. coli*.

6. A method for preparing nanoparticles of quantum dots, the method comprising the steps of: culturing a microorganism transformed with an expression vector containing a gene encoding a heavy metal-binding protein, wherein the heavy metal-binding protein is phytochelatin synthase, in a heavy metal-containing medium, to produce heavy metal quantum dots in the microorganism; and collecting the produced heavy metal structures, wherein the expression vector containing a heavy metal-binding protein-encoding gene is pTJ1-AtPCS having a cleavage map of FIG. 2 or pTJ1-PpMT having a cleavage map of FIG. 3.

7. The method for preparing nanoparticles of heavy metal quantum dots according to claim 1, wherein the microorganism is selected from the group consisting of gram-positive bacteria, gram-negative bacteria, Actinomycetes, and fungi.

8. The method for preparing nanoparticles of heavy metal quantum dots according to claim 1, wherein the microorganism is *E. coli*.

9. The method for preparing nanoparticles of heavy metal quantum dots according to claim 6, wherein the heavy metal is one or more selected from the group consisting of cadmium (Cd), zinc (Zn), selenium (Se), tellurium (Te), cesium (Cs), copper (Cu), lead (Pb), nickel (Ni), manganese (Mn), mercury (Hg), cobalt (Co) and chromium (Cr).

* * * * *

UNITED STATES PATENT AND TRADEMARK OFFICE
CERTIFICATE OF CORRECTION

| | | |
|---|---|---|
| PATENT NO. | : 8,476,055 B2 | Page 1 of 1 |
| APPLICATION NO. | : 12/301581 | |
| DATED | : July 2, 2013 | |
| INVENTOR(S) | : Sang Yup Lee et al. | |

It is certified that error appears in the above-identified patent and that said Letters Patent is hereby corrected as shown below:

In the Claims:

Column 14, Line 49: change "metal structures, wherein the expression vector containing a" to --metal quantum dots, wherein the expression vector containing a--

Signed and Sealed this
Eighteenth Day of March, 2014

Michelle K. Lee
*Deputy Director of the United States Patent and Trademark Office*

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1
ggaattcatg gctatggcga gtttat                                    26

<210> SEQ ID NO 2
<211> LENGTH: 31
<212> TYPE: DNA
<213> ORGANISM: Artificial Sequence
<220> FEATURE:
<223> OTHER INFORMATION: Synthetic Construct

<400> SEQUENCE: 2
cccaagctta ttaataggca ggagcagcga g                              31

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
ggaattcatg aacgatcaac gctgcgc                                   27

<210> SEQ ID NO 4
<211> LENGTH: 29
<212> TYPE: DNA
<213> ORGANISM: Artificial Sequence
<220> FEATURE:
<223> OTHER INFORMATION: Synthetic Construct

<400> SEQUENCE: 4
aactgcagtt agggcgagat cggatcact                                 29

<210> SEQ ID NO 5
<211> LENGTH: 1458
<212> TYPE: DNA
<213> ORGANISM: Arabidopsis thaliana

<400> SEQUENCE: 5
atggctatgg cgagtttata tcggcgatct cttccttctc ctccggccat cgactttttct    60 tccgccgaag gcaagctaat cttcaatgaa gcgcttcaga aggaactat ggaaggattt    120 ttcaggttga tttcgtattt tcagacacaa tccgaacctg cgtattgtgg tttggctagt    180
ctctcagtgg tgttgaatgc tctttctatc gatcctggac gtaaatggaa agggccttgg    240
aggtggtttg atgaatcaat gttggattgc tgcgaacctc tggaagtagt gaaggaaaaa    300
ggcatttcat ttggaaaagt tgtctgtttg gctcattgtt caggagcaaa agttgaggct    360
ttccgtacaa gtcagagcac cattgatgat ttccgcaaat tgtcgtcaa atgcacgagt    420 tctgagaatt gtcatatgat ctcaacatat caccgaggtg tatttaagca gactgggact    480
ggtcactttt cacctattgg tgctataat gctgagagag atatggcttt gattcttgat    540
gttgctcgtt tcaagtatcc ccctcactgg gttcctctta aacttctttg ggaagccatg    600

```
-continued gacagtattg atcagtcaac agggaaacgt agagggttca tgctcatatc tagaccacac      660
agagaacccg gattgctcta tactctgagc tgcaaggatg aaagctggat cgaaatagcc      720
aagtatttga aggaagatgt tcctcgtctt gtaagttcac agcatgtaga ttctgtggag      780
aaaatcatat cagttgtgtt caagtcactt ccatcaaatt tcaaccaatt catcagatgg      840
gtggctgaga tccgaattac agaggactca aaccaaaatc tcagcgcaga ggcgaagtct      900
aggctgaaac taaagcaatt ggtgctgaag gaagtgcacg aaactgaact gttcaaacac      960
atcaataagt tcttatccac agtgggttat gaagacagtc tgacttatgc tgctgcaaag     1020
gcttgttgcc aaggagctga aatcttatcc ggaagcccat caaaagagtt ttgttgtcgg     1080
gaaacttgcg tgaaatgcat caaaggtcct gatgactctg aaggcacggt ggtgaccgga     1140
gttgtggtgc gtgatgggaa tgaacaaaag gttgatctgt tagtgccatc gacgcaaact     1200
gagtgtgaat gtggtcctga agcaacttat ccagcaggaa acgatgtgtt cactgcactt     1260
ctattggctt tacctccaca gacatggtca gggatcaaag accaagctct tatgcatgaa     1320
atgaagcagc tcatttccat ggcttccctc ccaactttgc ttcaagaaga ggtattgcat     1380
cttcgacggc aacttcagct gctaaaacga tgccaagaga acaaggaaga ggatgatctc     1440
gctgctcctg cctattaa                                                   1458

<210> SEQ ID NO 6
<211> LENGTH: 225
<212> TYPE: DNA
<213> ORGANISM: Pseudomonas putida KT2440

<400> SEQUENCE: 6
atgaacgatc aacgctgcgc gtgtacgcac tgttcctgca ctgtggatgc caatgccttg       60
cagcgcgacg gcaaggccta ttgctgcgag gcctgcgcca gcggccaccg caagggtgag      120
ccctgccgga tgcaggactg ccattgtggt gagaagccgg gcgagagcgc ggtggacaat      180
gcgttggatg aaaccttccc agcgagtgat ccgatctcgc cctga                      225
```